US012389981B2

(12) United States Patent
Brass et al.

(10) Patent No.: US 12,389,981 B2
(45) Date of Patent: Aug. 19, 2025

(54) FOOTWEAR HAVING AN ELASTIC CORRECTING STRAP FOR TREATING AND PREVENTING FOOT MALPOSITIONS

(71) Applicant: Hallufix AG, Grünwald (DE)

(72) Inventors: Manfred Brass, Grünwald (DE); Franz Fischer, Amberg (DE)

(73) Assignee: HALLUFIX AG, Grünwald (DE)

( * ) Notice: Subject to any disclaimer, the term of this patent is extended or adjusted under 35 U.S.C. 154(b) by 0 days.

(21) Appl. No.: 18/553,366

(22) PCT Filed: Mar. 30, 2022

(86) PCT No.: PCT/EP2022/058388
§ 371 (c)(1),
(2) Date: Sep. 29, 2023

(87) PCT Pub. No.: WO2022/207691
PCT Pub. Date: Oct. 6, 2022

(65) Prior Publication Data
US 2024/0164475 A1  May 23, 2024

(30) Foreign Application Priority Data

Mar. 30, 2021  (DE) .................. 10 2021 108 100.9

(51) Int. Cl.
A43B 7/26 (2006.01)
A43B 3/12 (2006.01)
A43B 7/14 (2022.01)

(52) U.S. Cl.
CPC .............. *A43B 7/14* (2013.01); *A43B 3/126* (2013.01); *A43B 7/26* (2013.01)

(58) Field of Classification Search
CPC .............. A43B 7/26; A43B 3/12; A43B 3/126
(Continued)

(56) References Cited

U.S. PATENT DOCUMENTS 1,349,095 A * 8/1920 Parisi .................. A43B 7/26
36/94
2,096,500 A * 10/1937 McCahan .............. A43B 3/128
36/94
(Continued)

FOREIGN PATENT DOCUMENTS

CN  111387636 A  7/2020
EP  3 716 806 B1  10/2020

OTHER PUBLICATIONS

German Search Report issued for the corresponding German application DE 10 2021 108 100.9; 12 pages, dated Jan. 18, 2022.
(Continued)

*Primary Examiner* — Marie D Bays
(74) *Attorney, Agent, or Firm* — Ruggiero McAllister & McMahon LLC

(57) ABSTRACT

Footwear for treating and preventing foot malpositions, in particular for treating and preventing hallux valgus, comprising a holding element configured for securing a foot relative to the footwear; and a tensioning element configured to be fastened to a toe and configured, in a state in which the footwear is fastened to the foot, to exert a first corrective force on the toe and to exert a second corrective force directed opposite to the first corrective force on a metatarsophalangeal joint of the toe, wherein the tensioning element is an elastic correcting strap.

17 Claims, 3 Drawing Sheets

(58) Field of Classification Search
USPC .......................................................... 36/11.5
See application file for complete search history.

(56) References Cited

U.S. PATENT DOCUMENTS

| | | | | |
|---|---|---|---|---|
| 2,575,868 | A * | 11/1951 | Ferri | A43B 7/26 36/94 |
| 3,066,678 | A * | 12/1962 | Riecken | A43B 7/26 D2/918 |
| 3,275,002 | A * | 9/1966 | Scholl | A43B 3/126 36/11.5 |
| 4,745,927 | A * | 5/1988 | Brock | A61F 5/019 36/94 |
| 4,813,162 | A * | 3/1989 | Harris | A43B 7/141 36/43 |
| 8,832,971 | B2 * | 9/2014 | Heid | A43B 7/145 36/94 |
| 10,506,844 | B1 * | 12/2019 | Zhurba | A43B 5/12 |
| 11,185,433 | B2 * | 11/2021 | Brass | A43B 7/26 |
| 2007/0074334 | A1 * | 4/2007 | Steel | A41B 11/004 36/9 R |
| 2007/0130796 | A1 * | 6/2007 | Iwata | A61H 11/00 36/94 |
| 2008/0005932 | A1 * | 1/2008 | Zitin | A43B 7/26 36/94 |
| 2011/0061262 | A1 * | 3/2011 | Krauss | A61F 5/14 36/43 |
| 2011/0130695 | A1 | 6/2011 | Rafique | |
| 2011/0173843 | A1 * | 7/2011 | Bishop | A43B 3/105 36/94 |
| 2011/0179674 | A1 * | 7/2011 | Heid | A43B 7/20 36/11.5 |
| 2015/0374094 | A1 * | 12/2015 | Gift | A43B 23/081 36/94 |
| 2019/0321209 | A1 * | 10/2019 | Hatzis | A61F 5/14 |
| 2020/0229531 | A1 * | 7/2020 | Driscoll | A43B 3/122 |
| 2021/0161246 | A1 * | 6/2021 | Lesser | A43B 7/26 |
| 2023/0147885 | A1 * | 5/2023 | Brass | A43B 7/00 36/94 |

OTHER PUBLICATIONS

International Search Report and Written Opinion for corresponding International (PCT) application PCT/EP2022/058388, 14 pages, dated Jun. 14, 2022.

* cited by examiner

FOOTWEAR HAVING AN ELASTIC CORRECTING STRAP FOR TREATING AND PREVENTING FOOT MALPOSITIONS

CROSS REFERENCE TO RELATED APPLICATIONS

This application is a national stage U.S. patent application of International Application No. PCT/EP2022/058388 filed on Mar. 30, 2022, and claims foreign priority to German Patent Application No. DE 10 2021 108 100.9, filed on Mar. 30, 2021, the entirety of each of which is incorporated herein by reference.

TECHNICAL FIELD

The invention relates to a footwear for treating and preventing foot malpositions, in particular for treating and preventing hallux valgus.

TECHNOLOGICAL BACKGROUND

Pathological malpositions in the metatarsal and forefoot area of a patient can have various causes, such as genetic predisposition, wearing wrong footwear, in particular shoes that are too tight or high-heeled, or a flattening of the longitudinal and transverse arch as a result of instability of the connective tissue in the metatarsal area. In particular, mispositioning of the big toe in the metatarsophalangeal joint, also known as hallux valgus, is gaining in importance due to steadily increasing number of cases.

Hallux valgus emerges from the metatarsophalangeal joint of the big toe being pulled in the direction of the inside of the foot by muscle traction. This causes the first metatarsal to protrude from the inside of the foot as a ball-shaped protrusion at the metatarsophalangeal joint, which is referred to as pseudoexostosis. In addition, hallux valgus is often accompanied by a change in the length and direction of traction of tendons, which can further exacerbate the deformity over time. As a result, arthrosis of the metatarsophalangeal joint of the big toe develops, which has to be treated surgically in advanced stages.

To stop or counteract the disease process, in addition to surgical interventions, the use of conservative therapy methods are known. For example, the use of tape bandages or orthoses are known for treating the foot in a resting position. Due to the required resting position of the foot during therapy, these devices are mainly used at night.

Furthermore, the use of sandals for therapeutic treatment of hallux valgus is known. For example, EP 3 716 806 A1 discloses a hallux valgus sandal having a tensile rigid loop section to be arranged around a toe to be treated, wherein therapeutic corrective forces act on the toe to be treated by exerting a tensile force on the loop section.

SUMMARY

Described is footwear for treating and preventing foot malpositions, which in particular enables effective therapeutic treatment and has a simple design.

Accordingly, a footwear is provided for treating and preventing foot malpositions, in particular for treating and preventing hallux valgus. The footwear comprises a holding element configured for securing a foot relative to the footwear; and a tensioning element configured to be fastened to a toe and configured, in a state in which the footwear is fastened to the foot, to exert a first corrective force on the toe and to exert a second corrective force directed opposite to the first corrective force on a metatarsophalangeal joint of the toe, wherein the tensioning element is an elastic correcting strap.

As the suggested footwear provides the first corrective force acting upon the toe and in addition the second corrective force acting upon the metatarsophalangeal joint, a particularly effective therapeutic treatment may be achieved. This is because the first and the second corrective force may simultaneously provide a therapeutic effect on the valgus position of the toe and on the *varus* position of the metatarsophalangeal joint. By doing so, the symptoms and the cause of the foot malposition can be treated simultaneously. The corrective forces acting on the foot and the associated therapeutic effects are described in more detail below in connection with the related components of the footwear.

The proposed solution further takes into account that, during walking, the toe and the metatarsophalangeal joint naturally tend to change their position relative to the metatarsus, in particular in a transverse direction of the foot, due to the flexion movement and due to loads acting thereon. In the context of the present disclosure, it has been found that these relative movements between the metatarsus, the toe and the metatarsophalangeal joint affect both the therapeutic effect and the wearing comfort of the footwear, in particular in case the footwear is used by a patient when walking for a longer period of time. To take this into account, the proposed footwear is equipped with the tensioning element provided in the form of an elastic correcting strap. The elastic correcting strap allows the footwear to be worn more comfortably by allowing, to a certain extent, the natural relative movements between the components of the foot, while continuing exerting the corrective forces. Further, the proposed footwear enables to make use of these relative movements to improve the therapeutic mode of action of the footwear. Specifically, as the forces exerted by the correcting strap depend on its elastic elongation, the use of the elastic correcting strap causes the amount of the corrective forces to be adapted during use. In this way, when pronounced relative movements occur, the amount of the corrective forces increases accordingly.

Compared to known devices, which are equipped with a multi-part tensioning mechanism generating corrective forces upon manually setting a tensile force on a toe loop section, the proposed footwear may be fixed to the foot at less efforts. In addition, the footwear may consist of fewer components and accordingly may have a compact and simple design.

The proposed footwear is intended to treat, counteract and/or prevent a pathological deformity of a foot, specifically a pathological malposition of a toe and/or a metatarsophalangeal joint, for example a metatarsophalangeal joint associated with the toe to be treated. Specifically, the proposed footwear may be used to prevent or treat hallux valgus, but is not limited to this application.

In the context of the present disclosure, a footwear refers to any type of shoe or shoe-like footwear. For example, the term "footwear" may refer to closed shoes and open shoes, such as sandals, in particular toe thong sandals, and the like. Accordingly, the proposed footwear is intended to be fastened to a foot of a patient and, in the state fastened to the foot, to act therapeutically on the foot, specifically on the toe and the metatarsophalangeal joint. In this context, the term "footwear" refers to both a pair of shoes, i.e. a pair consisting of a left shoe and a right shoe, and to a single shoe.

In the present disclosure, the term "in a/the state properly fastened to the foot", herein also referred to as "in the fastened state", refers to a state in which the footwear is purposefully fastened to a patient's foot and accordingly provides a desired therapeutic effect for correcting or preventing foot malposition.

The proposed footwear is provided and designed such that, in the fastened state, it exerts corrective forces on the foot. In the present disclosure, the term "corrective forces" refers to forces that have a therapeutic effect on the foot to be treated. Specifically, the corrective forces cause those parts of the foot affected by malposition to be pushed into an anatomically correct or intended position in order to achieve a desired therapeutic effect.

As set forth above, in the context of the present disclosure, it has been found that a particularly effective therapeutic effect may be achieved by exerting the second corrective force acting on the metatarsophalangeal joint in addition to the first corrective force acting on the toe. Specifically, in the context of the present disclosure, the feature defining that the "second corrective force is exerted on the metatarsophalangeal joint" relates to such corrective forces that act therapeutically on the metatarsophalangeal joint. Such corrective forces may be applied directly to the metatarsophalangeal joint by means of the correcting strap or directly to a sideways protruding portion of the toe ball, in particular a pseudoexostosis. Alternatively, such corrective forces may act indirectly on the metatarsophalangeal joint or the protruding portion of the toe ball by means of the correcting strap, for example by exerting a corrective force on a metatarsal, specifically the first metatarsal, in the region of the metatarsophalangeal joint. In particular, the second corrective force may have the specific purpose of acting therapeutically on the varus position of a metatarsal, in particular on the varus position of the first metatarsal. The thus resulting combination of corrective forces applied on the foot may be particularly beneficial when treating hallux valgus.

As set forth above, the second corrective force is directed opposite to the first corrective force. In the present disclosure, this is understood to mean that a vector representing the first corrective force is pointing in an opposite direction compared to a vector representing the second corrective force. As such, the vectors representing the first and the second corrective force are parallel to each other, but point in different directions and are particularly spaced apart.

In the following, in connection with the correcting strap, reference is generally made to a toe of the foot for the sake of simplicity. Specifically, the toe may refer to the big toe of the foot to be treated. However, the footwear is not limited to this application such that the term "toe" may also refer to, for example, the little toe. Accordingly, in connection with the second corrective force, reference is generally made to a metatarsophalangeal joint for the sake of simplicity, wherein by this term in particular the metatarsophalangeal joint of the big toe may be meant, although the footwear is not limited to this application. Alternatively, the term "metatarsophalangeal joint" may refer to, for example, the metatarsophalangeal joint of the little toe.

In the present disclosure, for specifying the footwear, in particular with respect to the foot to be treated, a reference system is used which is oriented to the midline or medial plane of a patient's body, as is common in anatomy. Thus, the position and direction of each component of the proposed footwear in the fastened state may be indicated with respect to the foot received in the footwear. Accordingly, the term "medial" refers to a direction or side of the footwear that points toward a medial plane of the wearer's body. In anatomy, the term "medial plane", also known as "midsagittal plane", generally refers to an anatomical plane that divides the body into two symmetrical parts. Accordingly, when describing a footwear, the term "in medial direction" means a direction pointing from the patient's foot to be treated towards his other foot. In this sense, the term "lateral" refers to a direction or side of the footwear that points away from the medial plane of the wearer's body. Accordingly, when describing a footwear fastened to one foot of the wearer, the term "lateral" means in a direction facing away from the other foot of the wearer.

For providing the corrective forces, the proposed footwear is equipped with the tensioning element provided in the form of an elastic correcting strap. The term "elastic strap", in particular "elastic correcting strap" and "elastic holding strap", is used in the present disclosure to mean a strap- or belt-shaped component which is elastically deformable to a certain, not negligible extent in order to generate the first and the second corrective force. This is a significant difference compared to a strap that is tensile rigid, i.e. non-elastic. For the application of the suggested footwear, those components are to be regarded as elastic which have a linear or non-linear elastic behavior for loads of at least 10% of the amount of the first or the second corrective force. In other words, the elastic correcting strap may absorb at least 10%, in particular substantially 100%, of the amount of the first or second corrective force in the form of tension forces induced by elastic deformation. In other words, the tension forces in the correcting strap induced by elastic deformation may be at least 10%, in particular substantially 100%, of the amount of the first or the second corrective force. In particular, the elastic correcting strap may be elastically deformable along its longitudinal direction and optionally along its transverse direction.

In particular, the proposed footwear is provided such that, in the state fastened to the foot, the elastic correcting strap is elastically deformed. In other words, the elastic correcting strap, in the state fastened to the foot, may be set in a tensioning condition in which it is elastically deformed and subjected to corresponding tensioning forces induced by elastic deformation. Yet, if the footwear is detached or decoupled from the foot to be treated, the correcting strap may be or may be set in a resting condition. In the state fastened to the foot, i.e. when the correcting strap is arranged in the tensioning condition, the elastic correcting strap may be elastically deformed to an extent of at least 2 mm or at least 3 mm or at least 5 mm. In other words, in the state fastened to the foot, i.e. when the correcting strap is arranged in the tensioning condition, a length of the correcting strap may be elongated due to elastic deformation by at least 2 mm or at least 3 mm or at least 5 mm compared to the resting condition of the correcting strap. Accordingly, the footwear may be designed and configured such that, in the fastened state, the first corrective force and/or the second corrective force are/is generated by a tensioning force prevailing in and induced by elastic deformation of the correcting strap.

The footwear can be configured and provided such that, in the state fastened to the foot, the correcting strap, at least in sections, lies against the foot, in particular in the region of the toe and/or in the region of the metatarsophalangeal joint, more particularly in the region of the sideways protruding portion of the toe ball. The surface of the correcting strap which lies against the toe and/or against the metatarsophalangeal joint, in particular against the sideways protruding portion of the toe ball, is referred to herein as engaging surface. The footwear may be designed such that, in the state fastened to the foot, the correcting strap is elastically deformed along its engaging surface, in particular along the entire length of the engaging surface, and/or along portions adjacent to the engaging surface.

The correcting strap may be built up from multiple layers, i.e. may have a multilayer structure. For example, the elastic correcting strap may have an elastically deformable layer, which may substantially contribute to the elastic property of the correcting strap. The elastically deformable layer may be provided by a rubber material, such as an elastomer. Alternatively or additionally, the correcting strap may comprise at least one lining layer. A first lining layer may be arranged along the engaging surface. The first lining layer may, for example, be made of a non-woven material, i.e. a fleece. By this configuration, the wearing comfort may be increased. According to one embodiment, the elastic correcting strap may be designed such that the first lining layer and a correspondingly designed second lining layer may be arranged on opposite sides of the elastically deformable layer.

In the fastened state, the correcting strap, at least partially, may engage around or grip around the toe. In the context of the present disclosure, the term "engaging around the toe" means that, in the fastened state, the correcting strap extends around the toe along its circumferential direction. The correcting strap can extend along the toe or along the toe and the metatarsophalangeal joint over a radian of substantially one It rad around the longitudinal axis of the toe. That is, the correcting strap extends circumferentially along at least one half of the circumference of a toe. In other words, the correcting strap may extend from one side of the toe to the opposite side of the toe or the metatarsophalangeal joint. According to one embodiment, the correcting strap may extend from a lateral side of the toe along a toe surface to a medial side of the foot in the region of the metatarsophalangeal joint or a toe ball. Alternatively, the correcting strap may extend from a medial side of the toe, specifically of a small toe, along a toe surface to a lateral side of the foot in the region of the metatarsophalangeal joint, specifically of the small toe. In other words, the engaging surface may be provided in the form of a turning surface, the orientation of which, i.e. whose surface normal, changes along the longitudinal axis of the toe and can point to the longitudinal axis of the toe.

The correcting strap may comprise a first end portion and an opposed second end portion, i.e. which is arranged at an opposite end compared to the first end portion. The footwear may be designed such that, in the state fastened to the foot, the first end portion is positioned between the toe and an adjacent further toe, in particular the second toe of the foot, and in particular is guided into a sole of the footwear. The second end portion may be positioned in the region of the metatarsophalangeal joint of the toe and may be guided into the sole. The second end portion may lie sideways against the metatarsophalangeal joint or against the sideway protruding portion of the ball of the toe associated with the metatarsophalangeal joint, and in particular may engage around a portion thereof. Alternatively, the second end section may be arranged in front of or after the metatarsophalangeal joint in a direction pointing from the metatarsophalangeal joint to the toe.

Further, the correcting strap may be connected, in particular firmly or fixedly connected and/or tensile rigidly connected, to the sole via the first end section and/or the second end section. For doing so, the first end section and/or the second end section may be form-fittingly connected and/or force-fittingly connected and/or adhesively connected to the sole. As such, the first and/or the second end section may protrude from an underside of the sole and may be accommodated in the sole, for example in a recess, or may be fastened to the underside of the sole in a tensile rigid manner. Alternatively, the first end section and/or the second end section may be guided into the sole and may be arranged between layers of the sole.

The sole may be built up from multiple layers, i.e. may have a multilayer structure. In other words, the sole of the footwear may be built up from multiple flat layers. For example, the sole may comprise at least two of the following elements: an outsole, a midsole, an insole, and an inlay sole. In particular, the sole may comprise an outsole and an insole, wherein the first end portion and/or the second end portion may be disposed in sections between the outsole and the insole.

In a further development, a connecting portion of the correcting strap, via which the first end portion of the correcting strap is connected to the sole, may be arranged spaced apart from a proximal end of a toe interspace between the toe and the adjacent further toe. A distance between the connecting portion and the proximal end of the toe interspace along a longitudinal foot axis may be in the range between 4 mm and 18 mm, in particular in the range between 6 mm and 15 mm.

Further, the footwear comprises the holding element configured to, in the fastened state, secure the foot to be treated relative to the footwear, in particular to hold the foot relative to the footwear in a predefined position. In other words, the holding element may be intended to exert a holding force on the foot in the fastened state of the footwear. Due to interaction of the corrective forces and the holding force, the footwear may be kept stable on the foot to be treated in a position intended for therapeutic treatment and simultaneously act therapeutically on the foot.

The holding element may comprise a holding strap which is configured to, in the state fastened to the foot, secure at least one further toe being arranged adjacent to the toe, in particular the second toe or the second to fifth toe, and/or a further metatarsophalangeal joint arranged opposed to the metatarsophalangeal joint, in particular the metatarsophalangeal joint of the little toe, relative to the footwear. In particular, the holding strap may exert a holding force on the further toe being arranged adjacent to the toe, wherein in particular the holding force may be directed opposite to the first corrective force, i.e. may point in an opposite direction compared to the first corrective force. In this way, the holding strap may ensure that the corrective forces may properly act on the toe and the metatarsophalangeal joint as the holding force may keep the foot stable in the footwear.

In a further development, the holding force, which is applied by the holding strap, may have a therapeutic effect on the foot to be treated, which in particular may contribute to the therapeutic effect of the first and the second corrective force and/or which may provide a different further therapeutic effect.

In the state fastened to the foot, the holding strap may lie against the further toe being arranged adjacent to the toe and/or may lie against the foot in the region of the further metatarsophalangeal joint being arranged opposed to the metatarsophalangeal joint. In a further development, in the state fastened to the foot, the holding strap may lie against the foot such that the holding strap extends from one side of the further toe, in particular the second toe, to an opposite side of the further metatarsophalangeal joint. In particular, the holding strap may extend from a medial side of the further toe, in particular the second toe, to a lateral side of the further metatarsophalangeal joint.

In particular, the holding strap may be an elastic holding strap which, in the state fastened to the foot, may be elastically deformed. More particularly, the holding strap may be elastically deformable along its longitudinal direction and optionally along its transverse direction. In other words, in the state fastened to the foot, the holding strap may be arranged or set in a tensioning condition in which it is elastically deformed and subjected to corresponding tensioning forces induced by elastic deformation. Yet, if the footwear is detached or decoupled from the foot to be treated, the holding strap may be or may be set in a resting condition. In the state fastened to the foot, i.e. when the holding strap is arranged in the tensioning condition, the elastic holding strap may be elastically deformed to an extent of at least 2 mm or at least 3 mm or at least 5 mm. In other words, in the state fastened to the foot, i.e. when the holding strap is arranged in the tensioning condition, a length of the holding strap may be elongated due to elastic deformation by at least 2 mm or at least 3 mm or at least 5 mm compared to the resting condition of the holding strap. Accordingly, the footwear may be designed and configured such that, in the fastened state, the holding force is at least partly generated by a tensioning force prevailing in and induced by elastic deformation of the holding strap.

In terms of its material properties, in particular with regard to its elasticity properties, the holding strap may be designed correspondingly to the correcting strap. In other words, the holding strap may be made of the same material as the correcting strap.

Alternatively or additionally, the holding element may comprise a further holding strap or an upper leather, also referred to as vamp, which, in the state fastened to the foot, secures a metatarsal region of the foot relative to the footwear and lies against the foot in the region of the instep. The further holding strap or the upper leather may be made of a material that is substantially tensile rigid. In other words, the further holding strap may be a tensile rigid holding strap or the upper leather may be a tensile rigid upper leather.

The further holding strap may comprise a distal end portion and two proximal end portions, which may be fixedly connected, in particular tensile rigidly connected, to the sole. The footwear may be designed such that, in the state fastened to the foot, the distal end portion is positioned between the toe and the adjacent further toe and is fastened to the sole, and the two proximal end portions are positioned on opposite sides, i.e. on a lateral side and a medial side, of the foot and fastened to the sole.

BRIEF DESCRIPTION OF THE DRAWINGS

Further implementations are explained in more detail below with reference to the Figures, which schematically show in.

DETAILED DESCRIPTION

Figure 1:
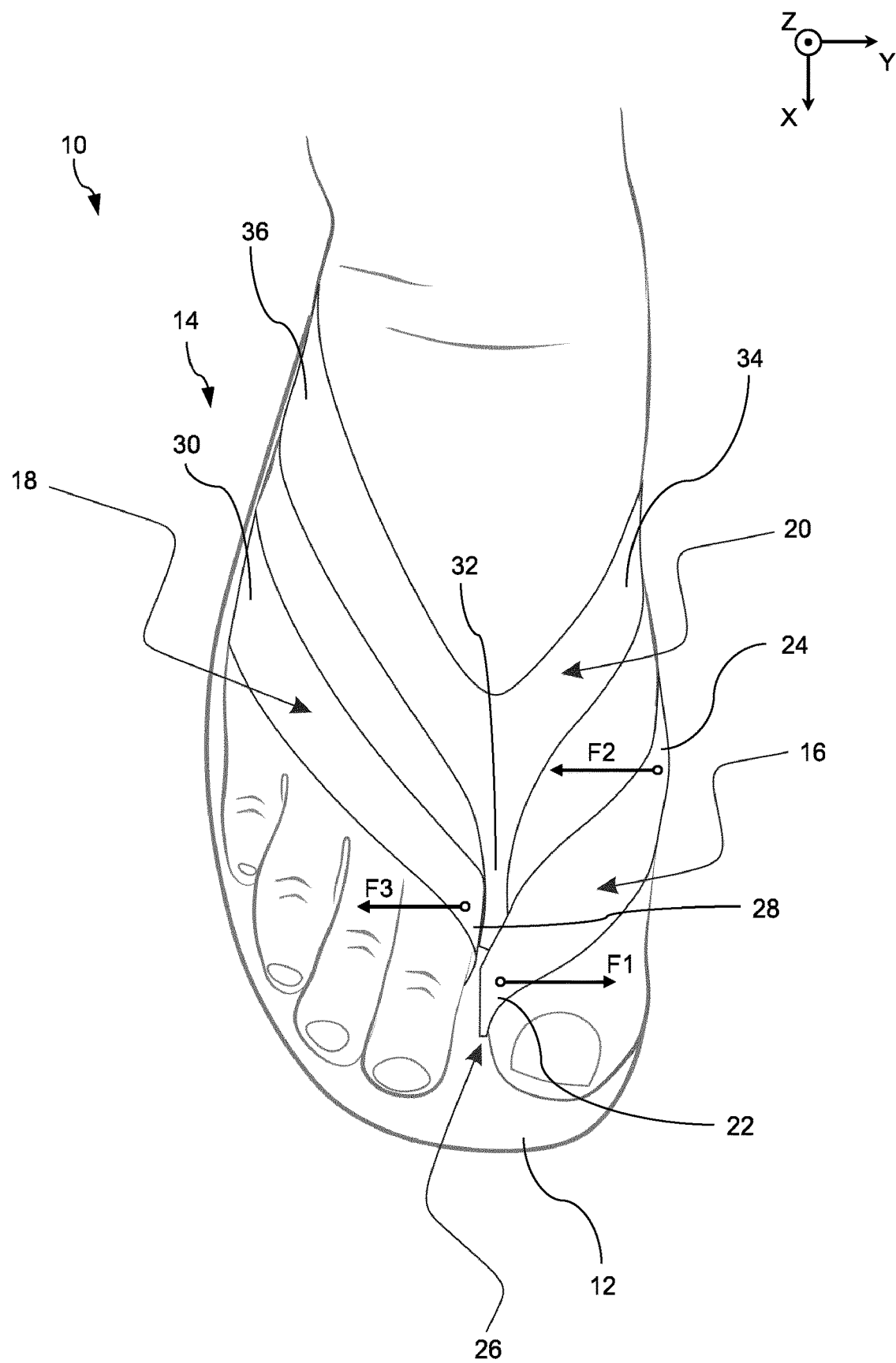
FIG. 1 a top view of a footwear for treating and preventing foot malpositions in a state fasted to a patient's foot.

In the following, embodiments are described on the basis of the Figures. In the Figures, identical, similar or similarly acting elements are denoted by identical reference numerals and a repeated description thereof may be omitted in order to avoid redundancies.

Figure 2:
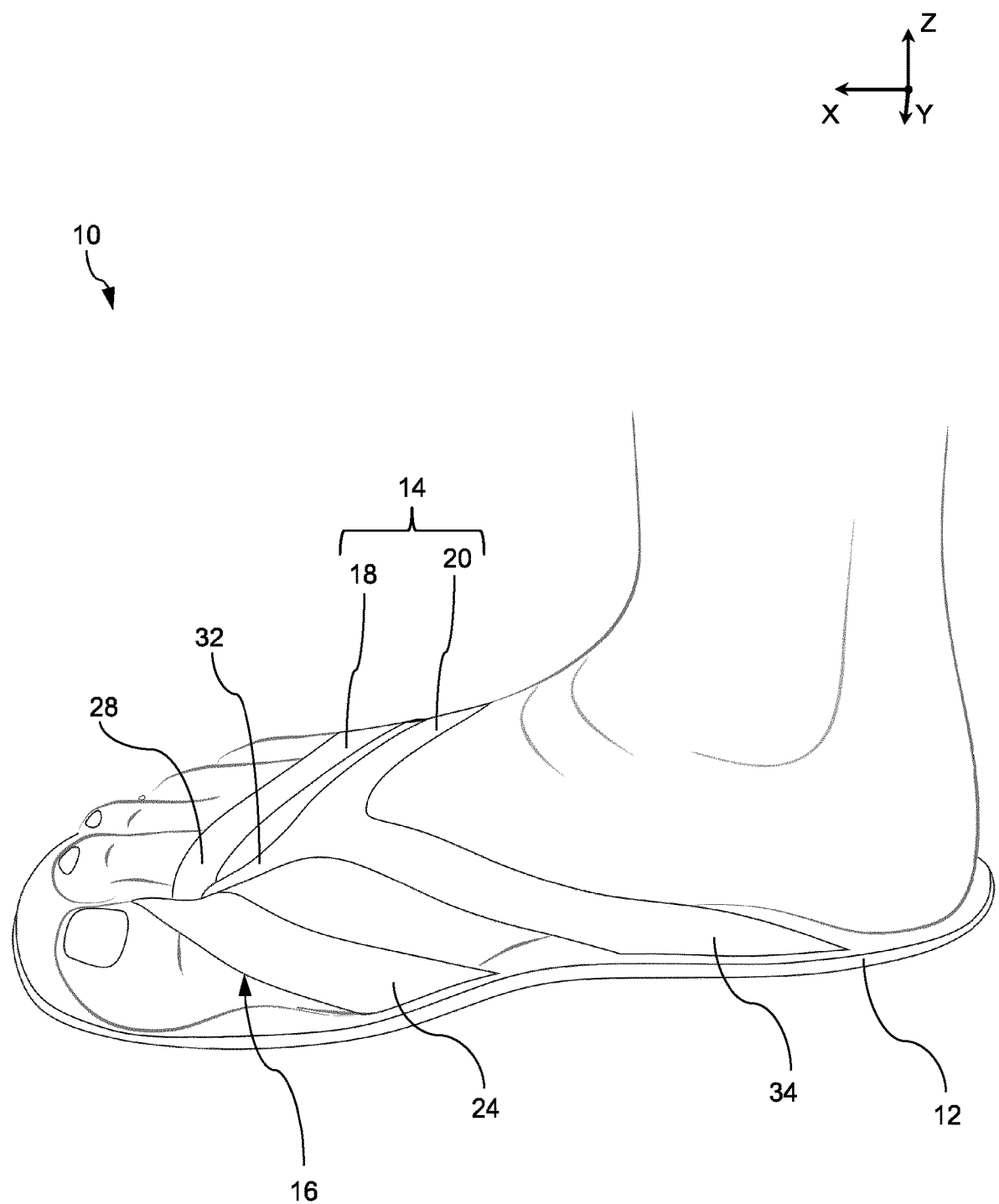
FIGS. 2 and 3 perspective views of the footwear depicted in FIG. 1 from different sides.
Figure 3:
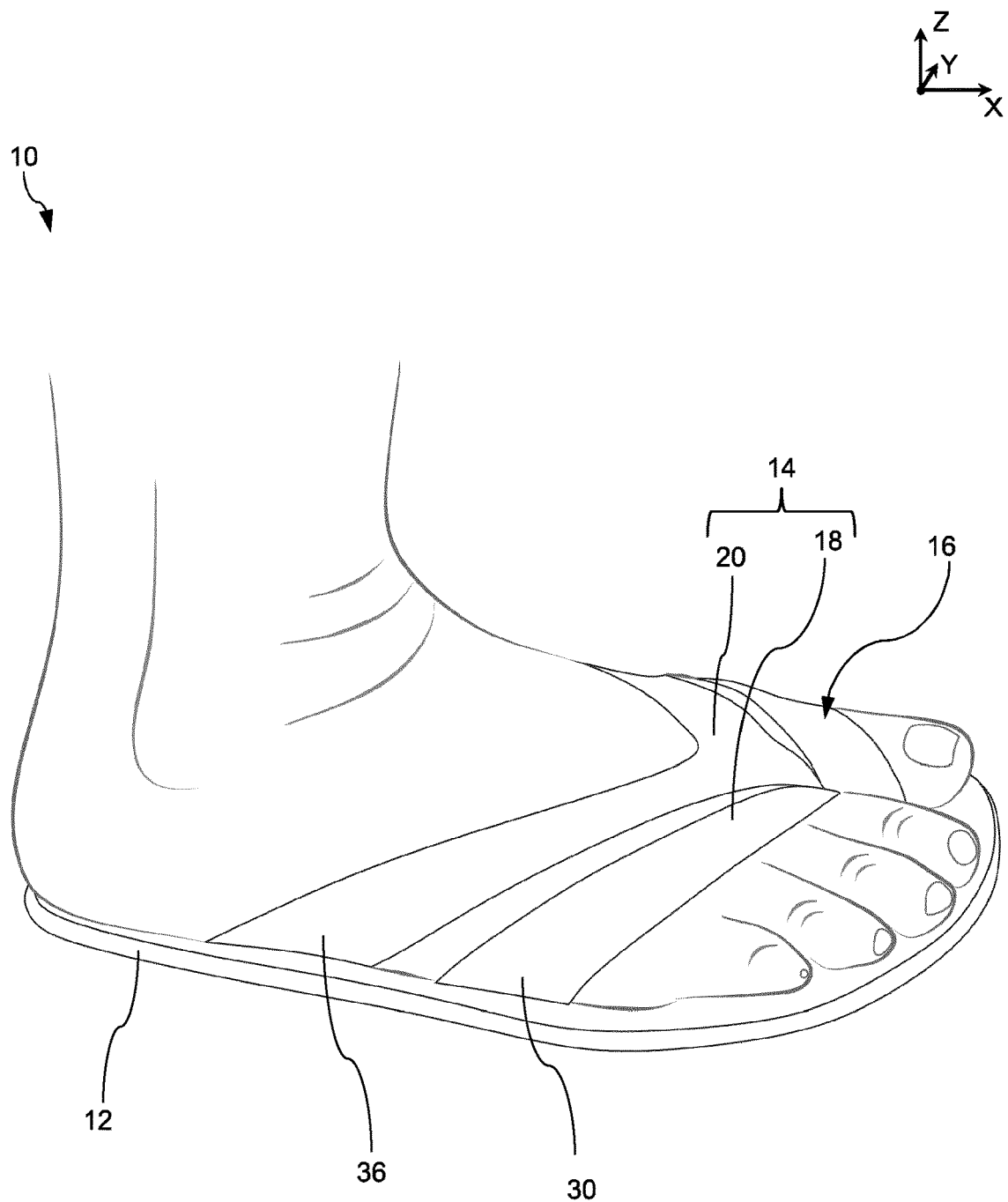

FIGS. 1 to 3 depict a footwear 10 for treating and preventing foot malpositions, in particular for treating and preventing hallux valgus. The footwear 10 is provided in the form of a sandal, in particular in the form of a toe thong sandal.

The footwear 10 comprises a sole 12 to which a holding element 14 and a tensioning element 16 are fastened, each forming a loop for receiving different portions of the foot to treated.

The tensioning element 16 is designed such that it forms a loop in which a big toe of the foot, hereinafter referred to as "toe", is received. The tensioning element 16 is configured to be fastened to the toe and to exert a first corrective force F1 on the toe and a second corrective force F2, directed in the opposite direction to the first corrective force, on a metatarsophalangeal joint of the toe, as indicated in FIG. 1 by vectors "F1" and "F2". The tensioning element 16 is provided in the form of an elastic correcting strap, hereinafter referred to as "correcting strap".

The holding element 14 is intended for fixing the foot relative to the footwear 10, in particular relative to the sole 12. For doing so, the holding element 14 comprises a first holding strap 18 and a separate second holding strap 20. The first holding strap 18 is designed such that it forms a loop in which a second to fifth toe of the foot is received, as can be gathered from FIG. 1. The first holding strap 18 is provided in the form of an elastic holding strap.

The second holding strap 20 is configured to, in the state fastened to the foot, secure a metatarsal region of the foot relative to the footwear 10. For doing so, the second holding strap 20 lies against the foot in the region of its instep, as can be gathered from FIGS. 1 to 3. The second holding strap 20 is provided in the form of a tensile rigid holding strap, i.e. a non-elastic holding strap.

The sole 12 of the footwear 10 is built up from multiple layers, i.e. is multi-layered, and comprises an outsole and an insole. The correcting strap 16, the first holding strap 18 and the second holding strap 20 are fixedly connected to the sole 12. For doing so, opposite end portions of the correcting strap 16, the first holding strap 18 and the second holding strap 20 are fixedly and tensile rigidly connected to the sole 12. More specifically, the opposite end sections of the correcting strap 16, of the first holding strap 18 and of the second holding strap 20 are guided into the sole and are arranged between and connected to the outsole and the insole in a form-fit and/or force-fit and/or adhesive manner.

In the state fastened to the foot, both the elastic correcting strap 16 and the first holding strap 18 are elastically deformed, in particular elastically deformed to an extent of at least 3 mm. In other words, in the state fastened to the foot, both the elastic correcting strap 16 and the first holding strap 18 are arranged in a tensioning condition in which they are elastically deformed and correspondingly are subjected to tightening forces which are induce by the elastic deformation. Yet, if the footwear is detached or decoupled from the foot to be treated, the correcting strap 16 and the first holding strap 18 are arranged in a resting condition. In the state fastened to the foot, i.e. when the correcting strap 16 and the holding strap 18 are arranged in the tensioning condition, the correcting strap 16 and the first holding strap 18 are elastically deformed to an extent of at least 2 mm or at least 3 mm or at least 5 mm. In other words, in the state fastened to the foot, a length, in particular a wrap or circumferential length, of the correcting strap 16 and the first holding strap 18 is elongated due to elastic deformation by at least 2 mm or at least 3 mm or at least 5 mm compared to their resting condition. In the fastened state, the first and the second corrective forces F1, F2 exerted by the correcting strap 16 and a holding force F3 exerted by the first holding strap 18 are generated by tension forces which prevail in the correcting strap 16 and the first holding strap 18 and which are induced by elastic deformation. In the shown configuration, the holding force F3 is exerted on the second toe in a direction opposite to the first corrective force, as can be gathered from FIG. 1.

The correcting strap 16 and the first holding strap 18 are built up from multiple layers. More specifically, they comprise an elastic layer, in particular made of an elastomer, which at opposing sides is covered by two lining layers. The lining layers are made of a non-woven material.

The correcting strap 16, along an engaging surface thereof, lies against the toe and the metatarsophalangeal joint. In the state fastened to the foot, the elastic correcting strap 16 is elastically deformed along its engaging surface and/or along portions adjacent to the engaging surface. In the tensioning condition, the correcting strap 16, at least in sections, engages around the toe such that the correcting strap 16 extends from a lateral side of the toe along a toe surface to a medial side of the foot in the region of the metatarsophalangeal joint, as can be gathered from FIGS. 1 and 2.

The correcting strap 16 includes a first end portion 22 and an opposite second end portion 24. In the state fastened to the foot, the first end portion 22 is positioned between the toe and an adjacent further toe, more specifically is positioned in a toe interspace therebetween. The second end portion 24 is positioned in the region of the metatarsophalangeal joint of the big toe, as can be gathered from FIG. 1. In the shown configuration, as set forth above, the correcting strap 16 is fixedly connected to the sole 12 of the footwear 10 via the first end portion 22 and the second end portion 24. The second end portion 24 lies sideways against the metatarsophalangeal joint, i.e. against the sideways protruding portion of the toe ball. Alternatively, the second end portion 24 may be arranged in front of or behind the metatarsophalangeal joint or the toe ball when looking in a direction pointing from the metatarsophalangeal joint to the toe, i.e. along the longitudinal direction X.

The first end portion 22 of the correcting strap 16 is connected to the sole 12 via a connecting portion 26. The connecting portion 26 forms a section of the correcting strap 16 which contacts or is guided into the sole 12. In other words, the first end portion 22 protrudes from the sole 12 and the connecting portion 26. The connecting portion 26 is arranged spaced apart from a proximal end of the toe interspace between the toe and the adjacent further toe such that a distance between the connecting portion 26 and the proximal end of the toe interspace along the longitudinal axis X is in the range between 6 mm and 16 mm.

The first holding strap 18 is configured to, in the state fastened to the foot, secure at least the second toe and the little toe metatarsophalangeal joint relative to the footwear 10. For doing so, the first holding strap 18 lies against the second toe and the little toe metatarsophalangeal joint. More specifically, the first holding strap 18 includes a first end portion 28 and an opposed second end portion 30. In the state fastened to the foot, the first end portion 28 is positioned between the big toe and the second toe, more specifically is positioned in the toe interspace provided therebetween. The second end portion 30 is positioned in the region of the small toe metatarsophalangeal joint, as can be gathered from FIG. 1. In the shown configuration, as set forth above, the first holding strap 18 is fixedly connected to the sole 12 of the footwear 10 via its first end portion 28 and its second end portion 30. In the shown configuration, the second end portion 30 lies against the foot such that it is arranged in front of the small toe metatarsophalangeal in the longitudinal direction X. Alternatively, the second end section 30 may be arranged behind the small toe metatarsophalangeal joint in the longitudinal direction X or lie sideways against it.

The second holding strap 20, which is substantially tensile rigid, i.e. non-elastic, includes a distal end portion 32 and two proximal end portions 34, 36 that are fixedly connected to the sole 12. The distal end portion 32 is disposed in the toe interspace between the big toe and the second toe and lies against the proximal end of the toe interspace. The two proximal end portions 34, 36 are positioned on opposite sides, more specifically on a lateral side and a medial side, of the foot and are fastened to the sole.

As far as applicable, all of the individual features illustrated in the above embodiments can be combined and/or interchanged without departing from the scope of the invention.

LIST OF REFERENCE NUMERALS 10 footwear
12 sole
14 holding element
16 tensioning element; correcting strap
18 first holding strap
20 second holding strap
22 first end section of the correcting strap
24 second end section of the correcting strap
26 connecting portion
28 first end section of the first holding strap
30 second end section of the first holding strap
32 proximal end section of the second holding strap
34, 36 distal end section of the second holding strap
F1 first corrective force
F2 second corrective force
F3 holding force

The invention claimed is:
1. Footwear for treating and preventing foot malpositions, comprising:
 a sole comprising an outsole and an insole;
 a holding element configured for securing a foot relative to the footwear; and
 a tensioning element configured to be fastened to a toe and configured, in a state in which the footwear is fastened to the foot, to exert a first corrective force on a toe and to exert a second corrective force directed opposite to the first corrective force on a metatarsophalangeal joint of the toe, the tensioning element comprising an elastic correcting strap, wherein
 the holding element comprises a holding strap and a further holding strap, wherein
  the holding strap is configured to, in a state in which the footwear is fastened to the foot, secure at least one further toe being arranged adjacent to the toe, a further metatarsophalangeal joint, or both, relative to the footwear, and
  the further holding strap, in a state in which the footwear is fastened to the foot, secures a metatarsal region of the foot relative to the footwear and lies against the foot in the region of its instep, and wherein oppositely arranged end sections of the correcting strap, the holding strap and the further holding strap are guided into the sole and arranged between the outsole and the in-sole and connected thereto in a form-fittingly and/or force-fittingly and/or adhesive manner.

2. The footwear of claim 1, wherein in the state fastened to the foot, the correction strap is elastically deformed.

3. The footwear of claim 1, which is configured such that, in the state fastened to the foot, the first corrective force, the second corrective force, or both are generated by a tensioning force prevailing in and induced by elastic deformation of the correcting strap.

4. The footwear of claim 1, wherein in the state of the footwear fastened to the foot, the correcting strap, along an engaging surface thereof, lies against the toe, the metatarsophalangeal joint, or both, and the correcting strap is elastically deformed along its engaging surface, along portions adjacent to the engaging surface, or both.

5. The footwear of claim 1, wherein in the state fastened to the foot, the correcting strap, at least in sections, engages around the toe such that the correcting strap extends from one side of the toe to an opposite side of the toe or the metatarsophalangeal joint.

6. The footwear of claim 1, wherein in the state fastened to the foot, the correcting strap lies against the foot such that the correcting strap extends from a lateral side of the toe along a toe surface to a medial side of the foot in the region of the metatarsophalangeal joint.

7. The footwear of claim 1, wherein the footwear is configured such that, in the state fastened to the foot, the first end portion is positioned between the toe and an adjacent further toe and the second end portion is positioned in the region of the metatarsophalangeal joint.

8. The footwear of claim 1, wherein the correcting strap is fixedly connected to a sole of the footwear via the first end portion and the second end portion.

9. The footwear of claim 1, wherein the second end portion lies sideways against the metatarsophalangeal joint or is arranged in front of or after the metatarsophalangeal joint in a direction (X) pointing from the metatarsophalangeal joint to the toe.

10. The footwear of claim 1, wherein a connecting portion of the correcting strap, via which the first end portion of the correcting strap is connected to the sole, is arranged spaced apart from a proximal end of a toe interspace between the toe and the adjacent further toe, wherein a distance between the connecting portion and the proximal end of the toe interspace along a longitudinal foot axis (X) lies in the range between 4 mm and 18 mm.

11. The footwear according to claim 1, wherein in the state fastened to the foot, the holding strap lies against or is arranged in the region of the further toe, or lies against or is arranged in the region of the further metatarsophalangeal joint, or lies against or is arranged in the region of both.

12. The footwear of claim 1, wherein the further holding strap is an elastic holding strap which is configured to be elastically deformed when the footwear is fastened to the foot.

13. The footwear of claim 1, wherein the holding strap is formed by a substantially tensile rigid holding strap.

14. The footwear of claim 2 wherein the correction strap is elastically deformable to an extent of at least 3 mm.

15. The footwear of claim 12 wherein the elastic holding strap is elastically deformable to an extent of at least 3 mm.

16. The footwear of claim 8, wherein the second end portion lies sideways against the metatarsophalangeal joint or is arranged in front of or after the metatarsophalangeal joint in a direction (X) pointing from the metatarsophalangeal joint to the toe.

17. The footwear of claim 10, wherein the holding element comprises a further holding strap configured for, securing at least one further toe adjacent to the toe, a further metatarsophalangeal joint, or both, relative to the footwear in the state of the footwear fastened to the foot.

* * * * *